United States Patent [19]

Broggi et al.

[11] 4,207,258
[45] Jun. 10, 1980

[54] PROCESS FOR THE PREPARATIN OF α-6-DEOXYTETRACYCLINES

[75] Inventors: Renato Broggi, Milan; Gino Cotti, Monza, both of Italy

[73] Assignee: Ankerfarm SpA, Milan, Italy

[21] Appl. No.: 772,923

[22] Filed: Feb. 28, 1977

Related U.S. Application Data

[63] Continuation of Ser. No. 333,382, Feb. 16, 1973, abandoned.

[30]   Foreign Application Priority Data

Feb. 24, 1972 [IT] Italy ................................ 20959 A/72

[51] Int. Cl.² ............................................ C07C 103/19
[52] U.S. Cl. ........................... 260/559 AT; 260/429 R
[58] Field of Search ................................... 260/559 AT

[56]   References Cited
PUBLICATIONS

Vol'Pin e. a., Russian Chem. Rev., Khimii, 1969, pp. 273–289.
Harmon e. a., Chem. Rev. 73 (1973), pp. 21–52.
Chatt e. a., J. Chem. Soc., 1964, pp. 508–513.
Osborn, J. Chem. Soc. (A), 1966, pp. 1711–1732.
Ugs, Aspects of Homogeneous Catalysts, vol. 1, 1970, pp. 24–29.

*Primary Examiner*—Arthur P. Demers
*Attorney, Agent, or Firm*—Stevens, Davis, Miller & Mosher

[57]   ABSTRACT

A process is provided for preparing alpha-6-deoxytetracyclines depicted by the formula:

wherein Y is H, F, Cl, Br or I; and R is H, OH or —O—CO—($C_{1-6}$ alkyl);

which comprises: contacting a 6-demethyl-6-deoxy-6-methylene tetracycline or salt thereof having the formula in which Y and R are as given above, with hydrogen at a temperature of between 15° C. and 80° C. in the presence of a catalyst soluble in a polar solvent, said catalyst being a complex of rhodium with electron donor ligands of a tertiary phosphine selected from the group consisting of triphenylphosphine, tributylphosphine, triethylphosphine, diethylphenylphosphine and diphenylethylphosphine and said polar solvent being a mono- or polyhydric alcohol with from 1 to 4 carbon atoms, N,N-dimethylformamide, N,N-dimethylacetamide, dioxan, tetrahydrofuran, methoxyethanol, ethoxyethanol, acetonitrile or pyridine.

13 Claims, No Drawings

PROCESS FOR THE PREPARATIN OF α-6-DEOXYTETRACYCLINES

This is a Continuation of application Ser. No. 333,382 filed Feb. 16, 1973, now abandoned.

The present invention relates to a process for the preparation of α-6-deoxytetracyclines by hydrogenation of the corresponding 6-demethyl-6-deoxy-6-methylenetetracyclines. More particularly, the process according to the invention is effected by means of a mechanism of homogeneous catalysis, such mechanism being based on the use of catalysts soluble in the reaction means.

Starting from a compound of the formula type

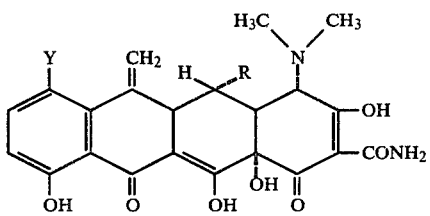

wherein
Y=H, F, Cl, Br, I
R=H, OH, -O-CO-R'
R'=C₁-C₆ alkyl or starting from a salt obtained from such a compound with a mineral or organic acid, or from a complex of such compounds with a polyvalent metal, there is obtained the α-isomer of the corresponding 6-deoxytetracyclines of the formula

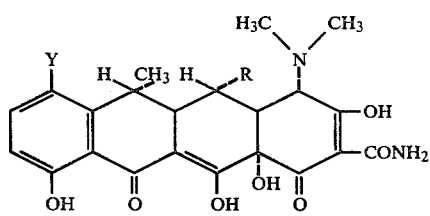

wherein
Y, R are as indicated above.

The compounds having the formula I can be prepared according to the processes described in British Pat. Nos. 951 663 and 995 031, U.S. Pat. No. 2,984,686 and German Patent No. 2 037 292.

The 6-Deoxytetracyclines are known antibiotics;

The present invention is based on the use of catalysts soluble in the reaction medium, consisting of coordination compounds of noble metals with electrondonor ligands.

Complexes of this type, and in particular those formed from Rh, Ru, Ir, Os, Pd, Pt, Ni with tertiary arsines, phosphines and stibines, are known in the literature as homogeneous catalysts for the selective hydrogenation of terminal carbon-carbon bonds.

Suitable ligands are: triphenylphosphine, triphenylarsine, triphenylstibine, tributylphosphine, triethylphosphine, diethylphenylphosphine, diphenylethylphosphine.

We have found that these complexes are active in the hydrogenation of exocyclic double bonds of the substrates of formula I, whereas the internal double bonds are not affected. Furthermore, the hydrogenation leads in selective manner to the formation of alpha isomers. The molecules of ligand can be easily replaced by those of the solvent in which the reaction takes place. Certain complexes with solvent molecules replacing the molecules of the ligands are so stable as to allow their isolation. Particularly indicated are the complexes of rhodium with triphenylphosphine, of the type RhCl(Ph₃P)₃, the dimer Rh₂Cl₂(Ph₃P)₄, the hydride and dihydride derivatives RhHCl₂(Ph₃P)₃, RhH₂Cl(Ph₃P)₃, and the complex Rh(Ph₃P)₃Cl₃ which are prepared according to methods described in literature (J. Chem. Soc.(A) (1966), 1711 and J. Chem. Soc.(A) (1966), 1670 and J. Chem. Soc. (1964) 2508).

In solution, the complex RhCl(Ph₃P)₃ can be partially dissociated and the following equilibrium can be obtained:

In the presence of hydrogen, more complex equilibria are formed:

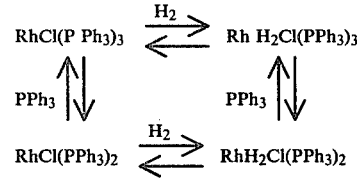

The mechanism of the fixation of the hydrogen and of the coordination of the olefin on the metal can be illustrated as follows:

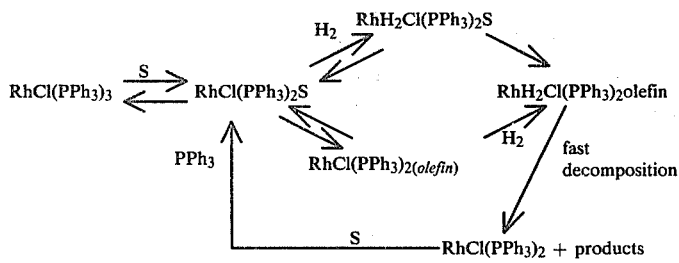

S represents a molecule of solvent. As the ligand, instead of triphenylphosphine use can be made of triethylphosphine or tributylphosphine or also of alkylphosphoric esters, triarylarsines or triarylstibines.

The ligand/metal molar ratio can vary from 1 to 4. The soluble catalyst can also be prepared directly in the reaction means by dissolving, in a suitable solvent the metal halide together with a number of moles of ligand, per mole of metal, greater than 1. According to the process of the present invention, a compound of the group of the tetracyclines having the general formula I and a catalytic amount of a complex of the aforementioned type, formed of a noble metal and an appropriate ligand, are dissolved in a suitable solvent and placed into contact with hydrogen at an appropriate temperature and pressure for a period of time sufficient to obtain total conversion into the hydrogenated compound.

At the end of the reaction, the product is separated from the solution by means of crystallization with very high yields of the alpha-6-deoxytetracyclines of the general formula II, while the homogeneous catalyst remains dissolved in the mother liquor.

Suitable solvents are: mono-or poly-hydric alcohols with from 1 to 4 carbon atoms, N,N dimethylacetamide, dioxan, tetrahydrofuran, methoxyethanol, ethoxyethanol, acetonitrile and pyridine. The speed of the reaction and the extent of the conversion depend to some degree on the temperature. At temperatures lower than 0° C. the reaction is too slow, while temperatures higher than 80° C. can cause decomposition of the starting substances. The preferred temperature range is 15°–80° C. Pressures can be used which are below 1 kg/cm$^2$, but the preferred operating range is from 1 to 150 kg/cm$^2$.

The reaction time required for a total conversion depends on temperature, pressure and type of catalyst used, but is generally within the range of from 1 to 8 hours. The preferred catalyst is RhCl(Ph$_3$P)$_n$, where n can be 2 or 3, because with this catalyst there are obtained almost total conversions into alpha isomers, which possess a greater biological activity, with the production of only negligible amounts of beta-isomers and slight traces of degradation products. Thin layer chromatography of the clear, crude reaction solution on completion of the hydrogenation shows that the ratio between the alpha and beta isomers is equal to or greater than 20:1, and that the percentage of degradation products does not exceed 2–3%. From final crude solutions of this kind, products of excellent quality have been isolated, with yields higher than 75%. As mentioned heretofore, the homogeneous catalyst can be prepared directly in the reaction means by dissolving the noble metal halide in the presence of a sufficient number of moles of ligand; the substrate is brought into solution and hydrogenation is carried out in the manner already described. For example, in the case of the complex of rhodium with a triphenylphosphine, if the number of moles of ligand is between 1 and 3 per mole of metal the same results are obtained as with the catalyst prepared separately. Amounts of ligand of less than 1 mole per mole of metal lead to the formation of deposits of metal in powder form which act as heterogeneous catalyst with prevalent formation of beta epimer. Amounts of ligand greater than 3 moles per mole of metal lead to homogeneous catalysts with gradually decreasing yields and incomplete conversions of the substrate; the stereospecificity remains high, in that there is prevalent formation of the alpha epimer along with the unaltered substrate, and the amount of beta epimer remains extremely low. The following non-limiting examples illustrate the present invention.

EXAMPLE I 10 g. of 6-demethyl-6-deoxy-6-methylene-5-oxytetracycline hydrochloride was dissolved in 1000 ml of methanol; 2.2 g. of complex RhCl(Ph$_3$P)$_3$ was added to the solution. The solution obtained was placed in autoclave and hydrogenated at 100 kg/cm$^2$ and at 40° C. for 4 hours. The autoclave was discharged, it being noted that the clear solution, light yellow in color, darkened rapidly. The thin layer chromatography (performed with kieselguhr coated plates buffered to pH 9, eluant water-acetone (1:10), U.V. light for detection) on the crude reaction solution gave the following result: alpha-6-deoxy-5-oxytetracycline≈95%; beta-6-deoxy-5-oxytetracycline<5%; slight traces of degradation products.

The solution was concentrated under vacuum; the product was crystallized by methanol while the catalyst remained dissolved in the mother liquor. With the use of standard techniques, a yield of 7.1 g. was obtained of 6-deoxy-5-oxytetracycline base, with spectrophotometric assay of 99.5%.

EXAMPLE II 4 g. of demethyl-6-deoxy-6-methylene-5-oxytetracycline hydrochloride, 0.5 g. of triphenylphosphine, 0.2 g. of RhCl$_3$.3H$_2$O were dissolved in 500 ml of methanol. With hydrogenation carried out as described in the Example I, a solution was obtained which was shown by thin layer chromatography to have the following composition; alpha-6-deoxy-5-oxytetracycline≈95%, beta epimer<5%, slight traces of degradation products.

The solution was concentrated to dryness, crystallized with methanol to remove the catalyst, and the base was prepared with a usual method. Yields: 2,9 g. of alpha-6-deoxy-5-oxytetracycline base, with spectrophotometric assay of 99,3%.

EXAMPLE III 5 g. of 6-deoxy-6-demethyl-6-methylene-5-oxytetracycline hydrochloride was suspended in 150 ml of N,N dimethylacetamide. 1.1 g. of the complex RhCl(Ph$_3$P)$_3$ was then added and hydrogenation was effected at 20 kg/cm$^2$ and 50° C. for 4 hours.

As the reaction progressed the solution became clearer and, on completion, there was obtained a clear solution from which there was isolated by known methods—3.5 g. alpha-6-deoxy-5-oxytetracycline base, having spectrophotometric assay of 99,2%.

EXAMPLE IV 2 g. of 6-deoxy-6-demethyl-6-methylene tetracycline hydrochloride was hydrogenated according to the method described in Examples 1 and 2, total conversion being obtained after 4 hours of reaction at 40° C. and 80 kg/cm$^2$. Chromatographic analysis showed a alpha epimer/beta epimer ratio of more than 20:1.

EXAMPLE V 2 g. of 6-demethyl-6-deoxy-6-methylene-5-acetoxy tetracycline and 0.4 g. of RhCl(Ph$_3$P)$_3$ was dissolved in dimethylformamide and hydrogenated at 35° C. and 20 kg/cm$^2$, for 4 hours. Thin layer chromatography performed on the solution obtained at the end of the reaction showed total conversion into alpha-6-deoxy-5-acetoxytetracycline.

What we claim is:

1. A process for the preparation of alpha-6-deoxytetracyclines of the formula:

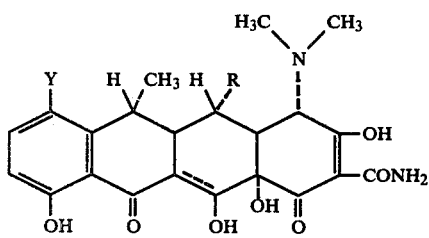

wherein

Y is H, F, Cl, Br or I; and

R is H, OH or —O—CO—($C_{1-6}$ alkyl);

which comprises contacting a 6-demethyl-6-deoxy-6-methylene tetracycline or salt thereof having the formula

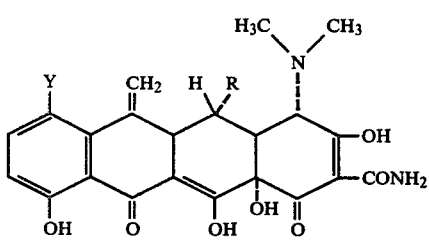

in which Y and R are as indicated above, with hydrogen at a temperature of between 15° C. and 80° C. in the presence of a catalyst soluble in a polar solvent, said catalyst being a complex of rhodium with electron donor ligands of a tertiary phosphine selected from the group consisting of triphenylphosphine, tributylphosphine, triethylphosphine, diethylphenylphosphine and diphenylethylphosphine and said polar solvent being a mono- or polyhydric alcohol with from 1 to 4 carbon atoms, N,N-dimethylformamide, N,N-dimethylacetamide, dioxan, tetrahydrofuran, methoxyethanol, ethoxyethanol, acetonitrile or pyridine.

2. The process according to claim 1, wherein said catalyst is RhCl($Ph_3P$)$_3$, RhCl($Ph_3P$), the dimer $Rh_2Cl_2(Ph_3P)_4$, the hydride derivative $RhHCl_2(Ph_3P)_3$, the dihydride derivative $RhH_2Cl(Ph_3P)_3$, or a solvate obtained from said complex with said polar solvent.

3. The process according to claim 1, wherein said catalyst is prepared directly in the reaction medium by reacting 1 mole $RhCl_3$ or $RhCl_3.3H_2O$ with 1 to 4 mole triphenylphosphine.

4. The process of claim 1 wherein said catalyst is prepared from a rhodium chloride and a triphenylphosphine.

5. The process of claim 1, wherein said catalyst is RhCl($Ph_3P$)$_2$S wherein Ph is a phenyl group and S is a molecule of said polar solvent.

6. A process of claim 1, wherein said 6-demethyl-6-deoxy-6-methylenetetracycline is 6-deoxy-6-demethyl-6-methylene-5-hydroxytetracycline or salt thereof.

7. A process of claim 6, wherein said salt is the hydrochloride of said 6-deoxy-6-demethyl-6-methylene-5-hydroxytetracycline.

8. A process of claim 1 conducted at a pressure of 1 to 150 kg/cm.

9. The process of claim 1 wherein said polar solvent is N,N-dimethylacetamide, N,N-dimethylformamide or methanol.

10. The process of claim 9 wherein said polar solvent is N,N-dimethylacetamide.

11. The process of claim 9 wherein said polar solvent is N,N-dimethylformamide.

12. The process of claim 9 wherein said polar solvent is methanol.

13. A process for the homogeneous catalytic hydrogenation of tetracyclines which comprises the step of treating a tetracycline of the formula

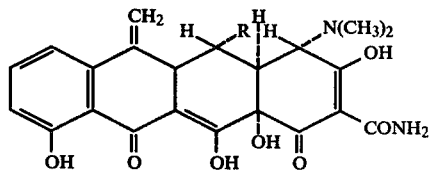

where R is H or OH with hydrogen in the presence of a catalyst of the formula Rh Cl ($Ph_3P$)$_3$ where Ph is phenyl at temperatures of between 15° C. and 80° C. at hydrogen pressures of from 1 to 150 Kg/cm² in a polar solvent selected from $C_1$-$C_4$ alcohols, N,N'-dimethylacetamide, dioxane, tetrahydrofuran, methoxyethanol, ethoxyethanol, acetonitrile, and pyridine.

* * * * *